United States Patent
Ashley et al.

(10) Patent No.: US 7,619,265 B2
(45) Date of Patent: Nov. 17, 2009

(54) MOLECULAR SINGLE ELECTRON TRANSISTOR (MSET) DETECTOR DEVICE

(75) Inventors: Timothy Ashley, Malvern (GB); Kevin M Brunson, Malvern (GB); Philip D Buckle, Malvern (GB); Timothy I Cox, Malvern (GB); Norman J Geddes, Malvern (GB); John H Jefferson, Malvern (GB); Russell A Noble, Malvern (GB); Ian C Sage, Malvern (GB); David J Combes, Malvern (GB)

(73) Assignee: QinetiQ Limited, London (GB)

( * ) Notice: Subject to any disclaimer, the term of this patent is extended or adjusted under 35 U.S.C. 154(b) by 278 days.

(21) Appl. No.: 10/577,734

(22) PCT Filed: Nov. 5, 2004

(86) PCT No.: PCT/GB2004/004699

§ 371 (c)(1),
(2), (4) Date: May 2, 2006

(87) PCT Pub. No.: WO2005/048350

PCT Pub. Date: May 26, 2005

(65) Prior Publication Data

US 2007/0134667 A1   Jun. 14, 2007

(30) Foreign Application Priority Data

Nov. 7, 2003   (GB) .................................. 0326049.4

(51) Int. Cl.
 *H01L 21/00*  (2006.01)
(52) U.S. Cl. ........................ 257/215; 257/253; 257/414; 257/E21.04; 438/49; 438/75; 977/807
(58) Field of Classification Search .................... 257/9, 257/215, 253, 414, E21.04; 977/721, 733, 977/806, 807; 438/75, 144, 48, 49
See application file for complete search history.

(56) References Cited

U.S. PATENT DOCUMENTS 5,646,420 A   7/1997   Yamashita (Continued)

FOREIGN PATENT DOCUMENTS

EP   0 668 500 A   8/1995

(Continued)

OTHER PUBLICATIONS

Feldheim et al., "Sensing Devices Using Chemically Gated Single Electron Transistors", PCT WO 01/13432 A1, Aug. 18, 2000 (Reference listed on IDS filed May 2, 2008.*
Cui, http://www.ccmicro.rl.ac.uk/info_microfluidics.html#2.2.3.*
International Search Report of PCT/GB2004/004699, mailed Sep. 7, 2005.
GB Search Report of GB 0326049.4, dated May 19, 2004.

(Continued)

*Primary Examiner*—Evan Pert
*Assistant Examiner*—Scott R Wilson
(74) *Attorney, Agent, or Firm*—Nixon & Vanderhye P.C.

(57) ABSTRACT

A molecular single electron transistor (MSET) detector device (14) is described that comprises at least one organic molecule (87) connecting a drain electrode (84) and a source electrode (82). In use, said at least one organic molecule (87) provides a quantum confinement region. At least one analyte receptor site (90, 92) is provided in the vicinity of said at least one organic molecule (87) that bind molecules of interest (analytes). A fluid analyser (2) is also described that includes the MSET detector, a pre-concentrator (4) and a fluid gating structure (6). The fluid gating structure (6) is arranged to selectively route fluid from the pre-concentrator (4) to either one of the detector (14) and an exhaust port (12). The pre-concentrator (4), fluid gating structure (6) and detector (14) are each formed as substantially planar layers and arranged in a stack or cube.

45 Claims, 6 Drawing Sheets

U.S. PATENT DOCUMENTS

| | | | | |
|---|---|---|---|---|
| 5,882,496 | A | * | 3/1999 | Northrup et al. ............ 204/601 |
| 6,171,378 | B1 | | 1/2001 | Manginell et al. |
| 6,586,787 | B1 | * | 7/2003 | Wu et al. .................... 257/288 |
| 2004/0219731 | A1 | | 11/2004 | Hartwich et al. |
| 2006/0154489 | A1 | * | 7/2006 | Tornow et al. .............. 438/745 |

FOREIGN PATENT DOCUMENTS

| | | |
|---|---|---|
| FR | 2 747 785 | 10/1997 |
| JP | 11-266007 | 9/1999 |
| WO | 97/39145 | 10/1997 |
| WO | 01/13432 A1 | 2/2001 |
| WO | 03/005369 A2 | 1/2003 |

OTHER PUBLICATIONS

Ikuta et al., "Fluid Drive Chips Containing Multiple Pumps and Switching Valves for Biochemcial IC Family", Proceedings IEEE $13^{th}$ Annual International Conference on Micro Electro Mechanical Systems, Jan. 23-27, 2000, pp. 739-744, XP010377220.

Becker et al., "Microreactors and microfluidic systems: an innovative approach to gas sensing using tin oxide-based gas sensors", Sensors and Actuators B, vol. 77, No. 1-2, Jun. 15, 2001, pp. 48-54, XP004246526.

* cited by examiner

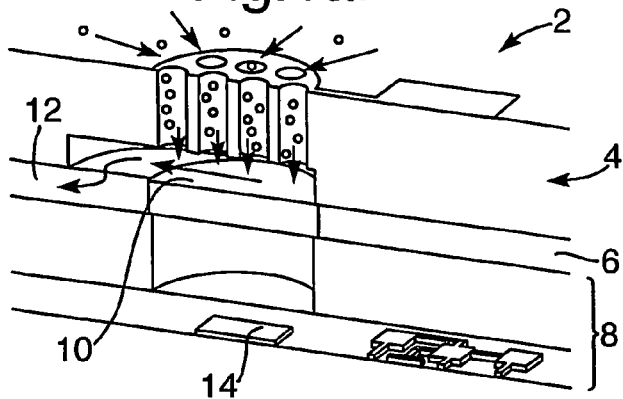
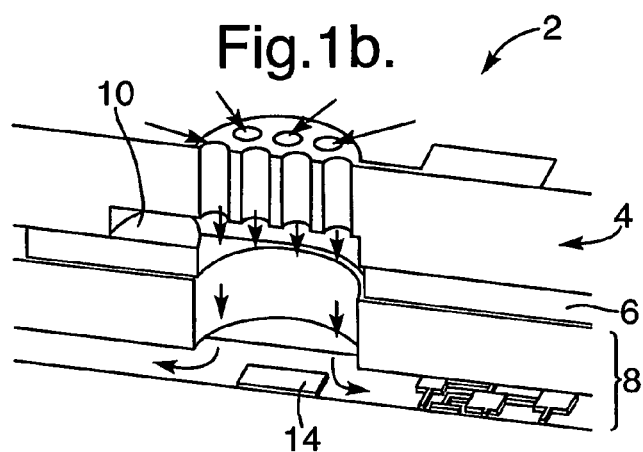
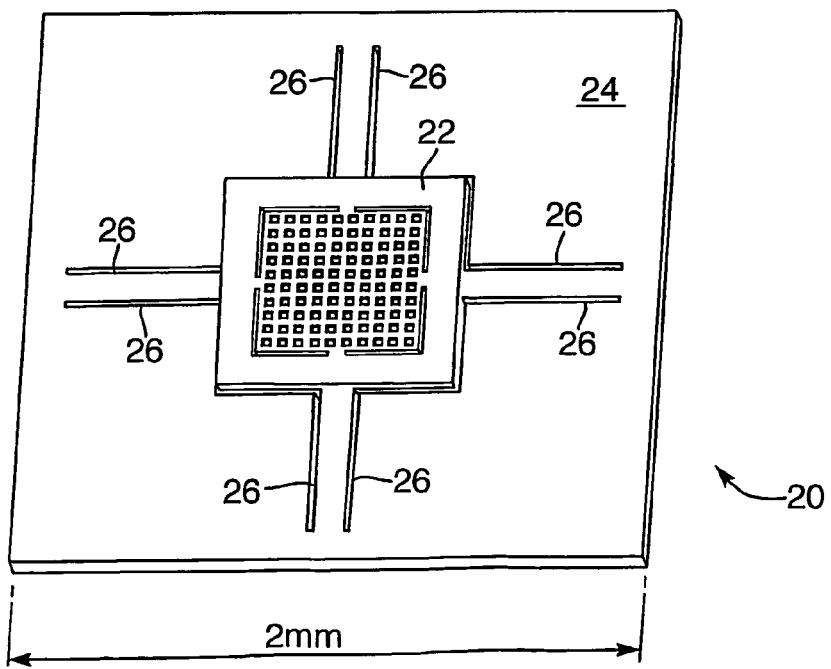

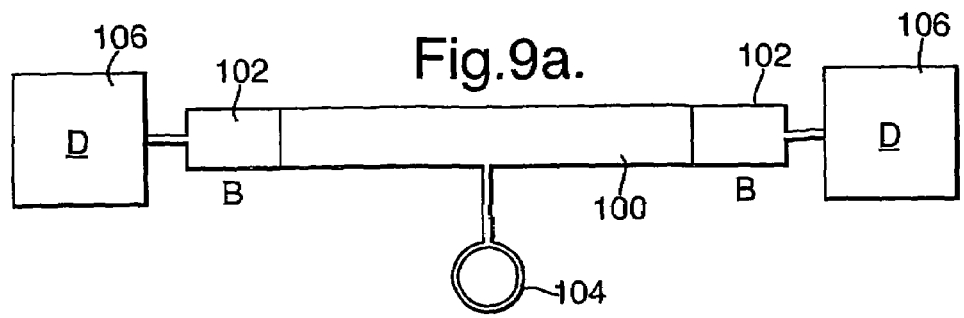
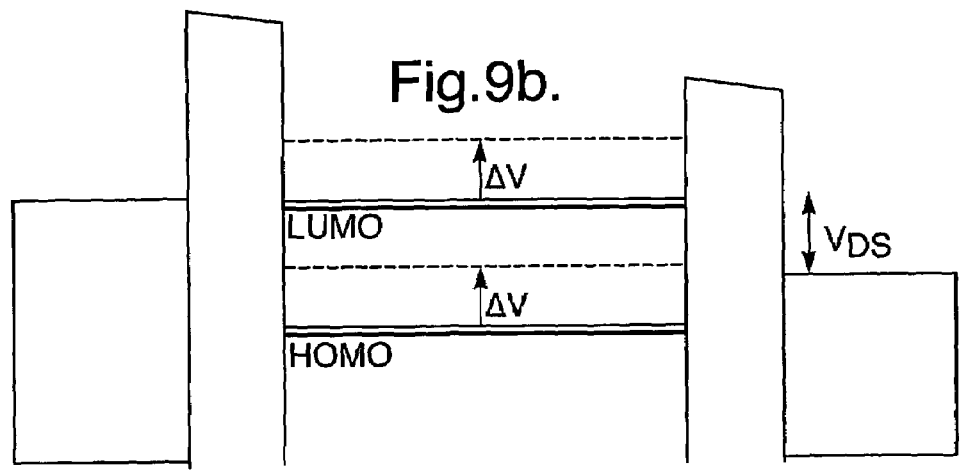
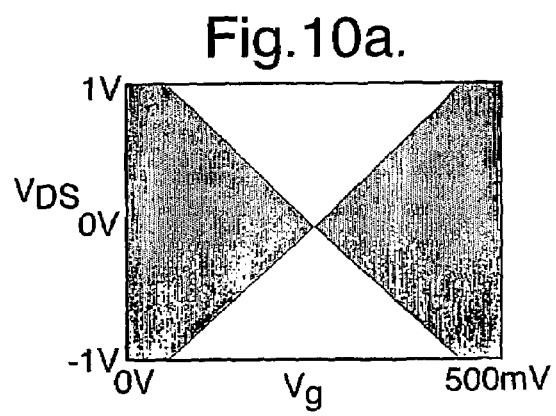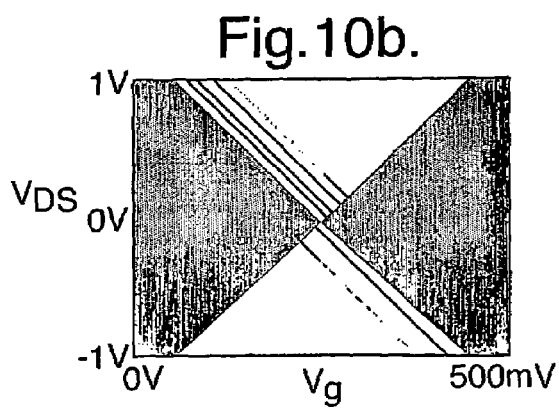

MOLECULAR SINGLE ELECTRON TRANSISTOR (MSET) DETECTOR DEVICE

This application is the U.S. national phase of international application PCT/GB2004/004699, filed 5 Nov. 2004, which designated the U.S. and claims priority of GB 0326049.4, filed 7 Nov. 2003, the entire contents of each of which are hereby incorporated by reference.

BACKGROUND OF THE INVENTION

1. Field of the Invention

The present invention relates to a fluid analysis apparatus. More particularly, the invention relates to fluid (especially gas) analysis apparatus that incorporates a molecular single electron transistor detector device.

2. Discussion of Prior Art

A variety of techniques are known for the detection and analysis of gas phase analytes. The standard techniques presently used to detect low molecular concentrations typically involve mass spectrometry used in conjunction with pre-concentration techniques and gas chromatography. In recent years, there has also been a drive to produce battery powered portable systems to enable in situ monitoring of, for example, industrial and volcanic emissions. However, such portable devices still weigh several kilograms and can have a somewhat limited sensitivity.

A number of so-called "pre-concentrators" are known that have been used to increase the sensitivity of gas analysis apparatus. The basic principle of a pre-concentrator is to collect molecules to be analysed (analytes) from a flow of gas. After a suitable collection period, the pre-concentrator is reconfigured (e.g. heated) such that the collected analytes are released in a smaller volume for subsequent analysis by an appropriate analyte detector.

An example of a pre-concentrator is described in U.S. Pat. No. 6,171,378 and also by G. Frye-Mason et. al. in the paper 'Hand-Held Miniature Chemical Analysis System (μChem-Lab®) for Detection of Trace Concentrations of Gas Phase Analytes', Micro Total Analysis Systems 2000, 229, 3 (2000). The pre-concentrator of G. Frye-Mason et. al comprises a thin film layer of adsorbent material carried on a substrate and has the benefit of inherently low thermal mass and high thermal isolation. However, a significant drawback of the device is that the essentially planar adsorbent layer provides a low interaction between the fluid and pre-concentrator and hence large adsorbing areas require a large die area.

Another example of a pre-concentrator is described by Wei-Cheng Tian et. al. in the paper entitled 'Microfabricated Preconcentrator-Focuser for a Microscale Gas Chromatograph', Journal of Microelectromechanical Systems, Vol. 12, No. 3, June 2003. This pre-concentrator comprises a plurality of channels defined, by deep reactive ion etching (DRIE), in high aspect ratio silicon. Commercially available adsorbent granules (e.g. Carbopack, Carboxen) of an appropriate particle size are located in the channels. Although such a structure provides an increased surface for a given substrate size, the flow of gas still passes over the bed, restricting its contact with the active surface of the adsorbent. Furthermore, the granules simply rest in the channels and are therefore not in intimate thermal contact with the heaters. The device of Wei-Cheng Tian et al thus requires considerable power to heat the adsorbent granules and is quite slow to respond.

A number of gas gating systems are also known for controlling the flow of gas through gas analysis apparatus. In particular, gas flow through a pre-concentrator must be controllably directed to either an exhaust port (e.g. when analytes are being collected by the pre-concentrator) or a detector (e.g. when the pre-concentrator releases adsorbed analytes). Typically, thermopneumatic valves based on diaphragm architectures have been used to provide the required gas flow control function.

Examples of thermopneumatic valves are described in Yang et al, "A MEMS Thermopneumatic Silicon Membrane valve", Proceedings of IEEE The Tenth Annual International Workshop on Micro Electro Mechanical Systems (MEMS '97), Nagoya, Japan, Jan. 26-30, 1997, pp. 114-118; Grosjean, C. et al "A practical thermopneumatic valve", Micro Electro Mechanical Systems 1999 (MEMS '99), Twelfth IEEE International Conference, 17-21 Jan. 1999 Page(s): 147-152); and J. S. Fitch et al "Pressure-based mass-flow control using thermopneumatically-actuated microvalves.", Proceedings, Solid-State Sensor and Actuator Workshop, pp. 162-165 (Transducers Research Foundation, Cleveland, Ohio, 1998).

Disadvantages of prior art thermopneumatic valves include the requirement for active actuation to hold such gas control valves in one of their positions (e.g. power must be continually applied to hold a normally open valve in the closed position). This leads to high power consumption, and thus a high energy budget. Furthermore, the flow of gas through such valves follows a convoluted route and the flow areas are restricted by the fundamental design of the device. Thermopneumatic valves also have a limited response speed and can suffer from hysteresis effects.

After the pre-concentration stage, analytes are released and carried through the gating stage to an appropriate detector. A number of miniature mass spectrometers are known; for example see J. Diaz et al "Sub-miniature double focusing sector field mass spectrometer for in situ volcanic gas monitoring", Am Soc. of Mass Spectrometry, Sanibel Island, Fla., January 2000 and J. J. Tullstall, et al "Silicon micromachined mass filter for a low power, low cost quadrupole mass spectrometer", Proceedings of The Eleventh Annual International Workshop on Micro Electro Mechanical Systems, 1998 (MEMS '98), 25-29 Jan. 1998, pp 438-442. Although such miniature mass spectrometers can provide the required analyte analysis, no system is known of truly sub-miniature proportions (e.g. having a volume less than 10 $cm^3$). The generation of suitable vacuum conditions to provide mass spectrometer operation remains a major miniaturisation obstacle.

In a completely unrelated technical field, it is also known that single electron transistor function may be provided by an organic molecule located between source and drain electrodes; see Kubatkin et al, "Single-electron transistor of a single organic molecule with access to several redox states", Nature, Vol. 425, 16 Oct. 2003. Kubatkin et al describes how the electrical characteristics of an MSET can be used to extract information about the electrical properties of the organic molecule from which the MSET is formed. The MSET described by Kubatkin et al comprises source and drain electrodes that are formed by condensing gold vapour on a substrate held at 4.2 Kelvin. The MSET structure is only operable at low temperature; at room temperature the gold source/drain electrode structures break down.

It is an object of the present invention to provide an improved detector device that mitigates at least some of the above mentioned disadvantages of known systems.

SUMMARY OF THE INVENTION

According to a first aspect of the present invention, a molecular single electron transistor (MSET) detector device comprises at least one organic molecule attached to a drain electrode and a source electrode wherein, in use, said at least one organic molecule provides a quantum confinement region (a so-called quantum dot), characterised in that at least one analyte receptor site is provided in the vicinity of said at least one organic molecule.

The present invention thus provides a molecular single electron transistor having at least one organic molecule located between a drain electrode and a source electrode. At least one analyte receptor site is additionally provided in the vicinity of the at least one organic molecule of the MSET for capturing molecules of interest (analytes). As described below, the at least one organic molecule of the MSET may comprises a side group that carries the at least one analyte receptor site and/or an analyte receptor site may be provided as part of an additional molecule that is located adjacent, but is not actually attached to, the at least one organic molecule of the MSET.

The electrical characteristics (e.g. the conductivity through the device as a function of source-drain voltage) of an MSET detector of the present invention are highly dependent on the electrical properties of the at least one organic molecule and also on the local electrical environment in which the at least one organic molecule is located. Consequently, a detectable change in the MSET electrical properties occurs when an analyte is retained by the at least one analyte receptor site. Furthermore, it has been found that analysis of the MSET electrical properties can not only determine the presence or otherwise of an analyte(s) but can also provide information on the electrical properties of a captured analyte thereby allowing different types of analyte to be distinguished. A detector of the present invention thus has a very high sensitivity allowing single molecules of interest (analytes) to be detected and even allowing the captured analytes to be identified.

Although molecular single electron transistors have been described previously by Kubatkin et al (ibid), the requirement for low temperature cryogenic operation that was previously reported would have made such devices unsuitable for chemical detection purposes. A molecular SET (MSET) of the present invention also provides a significantly more compact device than known mass spectrometer based analyte detection systems.

Advantageously, the at least one organic molecule comprises at least one analyte receptor site. For example, the at least one organic molecule of the MSET may have a side group which provides the at least one analyte receptor site. In other words, the at least one organic molecule of the MSET may feature specific functional groups (analyte receptor sites), which bind the molecule of interest thereby giving an observable change in MSET conductance Alternatively, or additionally, an analyte receptor site may be located adjacent, but not attached to, the at least one molecule. For example, the analyte receptor site may be carried by a molecule that is anchored to the substrate from which the single electron transistor is formed.

Preferably, the at least one organic molecule is an elongated conjugated organic molecule (i.e. a conjugated organic rod type molecule) having first and second ends. Conveniently, the first end of the elongated conjugated organic molecule is attached to the source electrode and the second end of the molecule is attached to the drain electrode. A self-assembled monolayer of organic molecules, for example conjugated organic rod molecules, may conveniently be located between the source and drain electrodes thereby connecting the source and drain electrodes. Preferably, a single organic molecule is attached to the source electrode and the drain electrode.

Advantageously, the at least one organic molecule is attached to the source and drain electrodes via tunnel barriers. The tunnel barriers may conveniently be provided by electrically insulating regions (e.g. insulating end chains) of said at least one organic molecule and/or the source and drain electrodes may carry an insulating material that forms the required tunnel barriers. Preferably, the device further comprises a gate electrode.

Advantageously, a first layer of material provides the source electrode and a second layer of material provides the drain electrode wherein said first and second layers sandwich, and are spaced apart by, a third layer of substantially insulating material.

Advantageously, a recess is provided in the third layer of substantially insulating material to provide a region between the source and drain electrodes in which the at least one organic molecule is located. In other words, the third layer of material is patterned, etched, deposited etc in some way to define a free space gap between the first and second layers. The gap between the source and drain electrode is substantially equal to the thickness of the third layer of substantially insulating material. After forming the gap, the at least one organic molecule is located within the gap between the source and drain electrodes thereby forming the MSET device.

In this manner, a reliable means for spacing the source and drain electrode apart is provided. Such a technique may provide source and drain electrodes that are accurately and consistently spaced apart by a few nanometres thereby reducing the complexity associated with forming electrode sets having the desired spacing. Furthermore, such electrode structures operate well at room temperature and do not significantly degrade with time.

Preferably, the thickness of the third layer of substantially insulating material is substantially equal to the length of the at least one organic molecule. The spacing between the source and drain electrodes can thus be accurately matched to the length of the at least one organic molecule of the MSET.

Conveniently, at least one of the first and second materials comprise semiconductor material. In other words, the source electrode and/or the drain electrode may conveniently be formed from a semiconductor material, such as silicon. The semiconductor material may be doped, with an "n" type or "p" type dopant, as necessary to provide the conductivity required to form the source and drain electrodes. Forming semiconductor source and drain electrodes of this type allows MSET operation at room temperature. This should be contrasted to prior art devices of the type described by Kubatkin et al (ibid) in which the gold electrodes contacting the organic molecule decompose at temperatures higher than around 150 Kelvin.

Advantageously, the semiconductor material comprises silicon. Preferably, the at least one organic molecule comprises end chains that will bind to silicon.

Preferably, the first layer of material comprises a silicon wafer, the second layer of material comprises polysilicon and the third layer of substantially insulating material comprises a silicon oxide. In a detector having a gate electrode, the wafer conveniently also carries a layer of polysilicon to form the gate electrode, the fourth layer being separated from the silicon wafer by a layer of silicon oxide. It would be appreciated that the layer of silicon oxide used to space apart the gate electrode from the silicon wafer may be deposited at the same time as deposition of the silicon oxide which spaces the drain electrode from the silicon wafer. Similarly, the polysilicon layers forming the gate and drain electrodes may be deposited in the same fabrication step.

Preferably, a complementary metal oxide semiconductor (CMOS) process (for example a standard 0.35 µm CMOS process) is used in the fabrication of an MSET device of the present invention. Such a process provides a suitable geometry for a MSET in the form of the gate oxide gap. Electrical contact with the at least one molecule can be made by using heavily doped Silicon contacts. The spacing between the source-drain contacts (i.e. the gap where the at least one molecule is attached) may be readily controlled down to monolayer accuracy. Once fabricated, the at least one organic molecule is attached to the source and drain electrodes.

The present invention thus enables an MSET to be formed using standard CMOS processing techniques. In the same process, any associated control and/or amplification circuitry may be fabricated. A single chip can thus be provided that comprises an integrated detection device with on-chip processing of the picoamp scale currents of the MSET. This will ensure good reproducibility in the fabrication process as compared with the hand-crafted processes using, for example, the deposition of gold particles. When combined with molecular self-assembly processes, arrays of MSETs can be manufactured with identical characteristics thereby offering, for example, built-in redundancy.

The device may advantageously comprise means for measuring MSET conductivity (i.e. the conductivity of the at least one organic: molecule) as a function of source-drain voltage. Alternatively, or additionally, the device may comprise means for measuring MSET conductivity as a function of gate voltage. A conductivity map as a function of gate voltage and source-drain voltage can thus be produced. The characteristics of such a map highlight so-called "quantization gaps" in the energy spectrum; these not only enhance the Coulomb blockade effect but also give rise to resonances in conduction that depend on the properties of the attached molecule. The provision of such a map can allow molecular identification of the analyte.

Conveniently, the device may further comprise integral electronic circuitry for measuring the conductance (e.g. as a function of source-drain and/or gate voltage) of the at least one organic molecule. If a CMOS process is used to form the device, the electronic circuitry may be formed during the process step that is used to form the source and drain electrodes.

According to a second aspect of the invention, a fluid analyser comprises an MSET device of the type described above. In this manner, a highly efficient detector of analytes present in a fluid (e.g. a liquid or gas) is provided.

Preferably, the analyser further comprising a pre-concentrator for releaseably retaining analytes from a fluid. Advantageously, the pre-concentrator comprises a layer of material having a plurality of apertures through which a fluid can be passed, the internal surfaces of said apertures being adapted to releaseably retain analytes from the fluid. Advantageously, the internal surfaces of the material forming the apertures may be adapted (e.g. by applying a coating or surface treatment) to releaseably retain (e.g. reversibly adsorb) molecules from a fluid. In other words, the internal surfaces of the apertures are arranged to absorb analytes from a fluid and to release such analytes when, for example, heated.

Conveniently, the internal surfaces of the apertures of the pre-concentrator are coated with adsorptive material. Alternatively, the surface of the apertures may be altered to provide the required adsorption properties. A multitude of surface chemistries can be generated to provide the required structure by, for example, vapour deposition of suitable materials, or the addition of suitable organic functional groups to the surface by standard techniques. For example, short chain polysiloxane molecules may be grafted onto the surface which, being hydrophobic, will reject water and offer some selective adsorption.

Conveniently, the internal surfaces defining the apertures of the pre-concentrator are porosified to enhance the effective surface area of the pre-concentrator. Alternatively, or additionally, the surface area of the pre-concentrator is enhanced by the direct application of a high capacity trapping matrix in thin film form (e.g. porous silicon dioxide films via sol gel processing and direct application of thin film polydimethylsiloxane, or PDMS).

Advantageously, the substrate comprises a layer of silicon, said apertures being formed through said layer of silicon. It is preferred to use Silicon to form the pre-concentrator layer because of the ease of manufacture and the ability to readily porosify the material. In addition, a variety of techniques are well known in the art for modifying the surface chemistry of silicon and its oxides by the addition of organic functional groups. However, the skilled person would appreciated that alternative materials may also be used; for example layers of material such as silicon dioxide, glass or polymers/plastics.

Conveniently, the layer of material of the pre-concentrator comprises a regular array of apertures which are advantageously arranged to form a honeycomb structure.

Passing a fluid through the apertures of such a honeycomb structure, rather than over a prior art pre-concentrator of the type described in U.S. Pat. No. 6,171,378, enables a much greater surface area to be placed into contact with the analyte carrying fluid. In the case of silicon, it has been found that the formation of a porous layer can increase the effective surface area by up to a factor of one hundred as compared with an untreated planar silicon wafer; this improvement multiplies with the factor of ten improvement available through the creation of a vertical honeycomb structure giving an overall adsorption enhancement factor of up to about one thousand. A more compact pre-concentrator can thus be provided.

Conveniently, the apertures are formed in the layer of material by deep reactive ion etching (DRIE). DRIE offers a convenient means for producing apertures in wafers of semiconductor material, such as silicon. For example, DRIE may be used to provide narrow apertures having a 30 µm diameter and a length of several hundred microns; such apertures ensure an efficient interaction of the fluid with the pre-concentrator surface. Aperture sizes of 5-100 µm diameter and 50-1000 µm length may be readily produced using such technology.

Furthermore, said layer of material may conveniently comprise a heater such as a heater element. The heater may be provided by forming a conductive region (e.g. by doping a semi-conductor) in the layer. The provision of integrated heaters will allow rapid heating of the internal surfaces of the apertures to release captured analyte. Alternatively, conductive tracks (e.g. metallic lines) may be formed on or in the layer. Discrete heater elements may also be attached to the layer. A heat sensor (e.g. a platinum track) may also be incorporated in to the layer of material so that the temperature of the first layer of material may be monitored.

The heated layer of material is preferably isolated from subsequent device layers and the package by including a thermal isolation layer (e.g. a glass interface) between the pre-concentrator and the underlying substrate (e.g. a gas gating chip). The low thermal conductance of such a material arrangement enables the achievement of fast response times.

Although a pre-concentrator of this type can advantageously be used as part of a analyser of the present invention, such a pre-concentrator may also be used as a component in a variety of alternative devices. In other words, a pre-concentrator can be provided for releaseably retaining analytes from a fluid, wherein the pre-concentrator comprises a layer of material having a plurality of apertures through which fluid can be passed, the internal surfaces of said apertures being adapted to releaseably retain analytes from a fluid.

Advantageously, the analyser may further comprise a fluid gating structure for controlling the flow of fluid from the pre-concentrator to the MSET device. Conveniently, the fluid gating structure is arranged to selectively route fluid from the pre-concentrator to either one of the MSET device or an exhaust port. This allows fluid under analysis to be passed through/over the pre-concentrator, which will releaseably retain analytes from the fluid, and routed to an exhaust port. After a suitable time period, the pre-concentrator can be arranged to release any captured analytes and the fluid gating structure can then be reconfigured to route fluid containing the released analytes to the MSET detector. In this manner, the fluid passed over the MSET will contain a greater density of analytes thereby increasing detection sensitivity.

Advantageously, the fluid gating structure comprises a substantially planar substrate and a shutter that is moveable in the plane of said substrate. The in-plane movement of the shutter is used to constrict the flow path to an outlet by, for example, covering the entrance aperture of that outlet. The provision of a shutter that moves in the plane of the substrate overcomes several disadvantages of the thermopneumatic devices of the prior art. For example, a MEMS type shutter can be more rapidly moved between the open and closed positions without suffering the temperature hysteresis effects reported in the literature for thermopneumatic valves. Furthermore, a MEMS shutter and associated actuation mechanisms can be formed from a single layer of a substrate (e.g. on a silicon wafer). Such an arrangement can thus be much smaller than the various prior art valves described above.

Conveniently, fluid is routed from the fluid gating structure to the MSET device along a channel having a long axis that is substantially perpendicular to the plane of the substantially planar substrate of the fluid gating structure. Fluid entering the fluid gating structure will thus impinge on the shutter from an orthogonal direction. Similarly, fluid that exits the device via an outlet can be arranged to pass along the same direction. In such a configuration, the shutter is not required to move against the force of the incident fluid when being moved in to, or out of, the fluid path. A smaller force can therefore be used by the actuation means associated with the shutter when moving between the open and closed positions. It would be appreciated that, in certain configurations, the fluid pressure may force the shutter into contact with the substrate from which it is suspended. In such a case, it may be necessary to reduce the fluid pressure when moving the shutter.

The shutter may advantageously be shaped such that it can engage and seal the entrance to the channel from the fluid gating structure to the MSET device. In this manner, the pressure of incident fluid on the shutter can actually be used to improve the seal. For example, a circular shutter may be provided in conjunction with a correspondingly circular entrance to the channel. In use, the shutter may be moved into the closed position and hence cover the entrance to the channel. Any applied fluid pressure may then force the shutter to tightly engage and seal the outlet. Furthermore, a raised annular sealing ring portion may also be provided around the circumference of the outlet. Engagement of the shutter with such a sealing ring can further improve the quality of the fluid seal.

The shutter may be arranged to adopt either one of an open position and a closed position, the open position allowing fluid to pass to the MSET detector device and the closed position preventing fluid from passing to the MSET device. Furthermore, the shutter may conveniently be retained, without the application of power, in an open position in which fluid is routed from the pre-concentrator to the MSET device or in a closed position in which fluid is routed from the pre-concentrator to an exhaust port.

As described above, when the shutter is in the closed position, any received fluid is directed to an exhaust port. Furthermore, when the shutter is in the open position, fluid may be advantageously prevented from flowing to the exhaust port. For example, the shutter, or another portion of the moveable member, may be arranged to block the exhaust port aperture when the shutter of the device is in the open position.

Conveniently, the fluidic pathway through the device when the shutter is in the open position is minimised. This reduces the possibility of analytes contained in a gas phase from becoming attached to portions of the fluid gating structure. Furthermore, it is advantageous for the dead space of the device (i.e. space within the device into which fluid can flow but not comprising part of the flow path) when in the open position to be minimised. Again, this prevents loss of analytes. A skilled person would appreciate that sealing arms could be provided to perform such a function. If analysing a non-volatile gas phase fluid, the device could also be heated to a suitable temperature to reduce or prevent condensation.

The shutter may also be held in any one of a plurality of intermediate positions to provide required flow control. For example, the relative proportion of fluid routed to the exhaust port and the MSET detector can be controlled as required. Furthermore, clamps or latches may be provided to hold the shutter in such open, closed or intermediate positions. This arrangement offers significant advantages over the prior art thermo-pneumatic valves described above which required the continual application of power to remain in one of the their states.

Advantageously, the shutter is a micro-electromechanical (MEMS) shutter. Conveniently, the moveable member comprises a MEMS electro-thermal actuation mechanism to impart movement to the MEMS shutter. Furthermore, it is preferred for the moveable member to comprise a MEMS compliant displacement mechanism; the amplitude of movement produced by the actuation mechanism can then be amplified to increase the amount of shutter travel that can be obtained. Herein, MEMS is taken to include micro-machined elements, micro-systems technology, micro-robotics and micro-engineering and the like.

Conveniently the planar substrate comprises silicon. For example, a silicon-on-insulator (SOI) wafer or the like may be used. Advantageously, the device is fabricated using a deep reactive ion etching (DRIE) process.

Although the invention can operate on any fluid (e.g. a liquid or a gas), it is preferred to use the fluid gating structure for gas based applications thus providing a gas flow controller. If a liquid is employed, the skilled person would appreciate the various sealing techniques that could be used to prevent the liquid from adversely affecting the operation of the device (e.g. by heat transport from electro-thermal actuation mechanisms etc) of the device.

The fluid gating structure described herein thus provides control over the flow of a received fluid to the MSET detector. Although such a gas gating structure is particularly suited to use in an analyser of the present invention, it should be noted that the fluid gating structure could also be advantageously used as a fluid control device in numerous alternative applications. In other words, a fluid device could be provided which comprises a first outlet and a moveable member, the moveable member providing control over the flow of a received fluid to the first outlet, wherein the device is formed from a substantially planar substrate and the moveable member comprises a shutter that is moveable in the plane of the substrate. Such a device may further comprise an exhaust outlet for receiving any fluid that is prevented, by said moveable member, from passing to said first outlet. In such a device, the fluid flow to the first outlet would be analogous to the fluid flow to the MSET device that is described above.

The present invention thus provides a fluid analyser in the form of a compact hybrid stack or "cube". For example, a three layer vertical stack may be provided that comprises a fluid gating structure that is sandwiched between the pre-concentrator layer and the detector layer. In use, an acquisition mode is first employed in which a fluid is passed through the pre-concentrator and directed, via the fluid gating device, to an exhaust port. In acquisition mode, the pre-concentrator is arranged to adsorb analytes and a high flow of fluid (e.g. air) across the pre-concentrator is desirable. After a predetermined period, the device is switched into detection mode. In detection mode, the pre-concentrator releases the captured analytes (e.g. by heating the adsorbent material) which are directed, via the fluid gating device, to the MSET detector for analysis. In detection mode, a low rate of fluid flow is preferably and an inert carrier fluid (e.g. argon gas) may advantageously be passed through the device.

Providing each analyser function (i.e. pre-concentration, fluid gating and detection) in a planar layer enables the device volume to be greatly reduced compared with prior art devices of the type described above. Furthermore, the flow path between each layer is significantly smaller than the flow path between the adjacent components of a prior art device thereby enhancing device sensitivity.

It should be noted that although such a compact cube arrangement is preferably implemented using the MSET detector, pre-concentrator and fluid gating structures described above it would be possible to form such a device using alternative components (e.g. a non-MSET based detector). In other words, a fluid analyser could be provided that comprises a pre-concentrator, a fluid gating device and a detector, the fluid gating device being arranged to selectively route fluid from the pre-concentrator to either one of the detector and an exhaust port, wherein the pre-concentrator, fluid gating device and detector are each formed as substantially planar layer and arranged in a stack.

Advantageously, the fluid analyser further comprises a pump to drive the fluid through the pre-concentrator and fluid gating device. The pump may have a variable power such that the fluid pressure can be increased or decreased as required. For example, a higher pressure may be required when the analyser is operating in acquisition mode compared with detection mode. Also, it may be advantageous to reduce fluid pressure (and hence the force against which any shutter or valve arrangement must operate) when the fluid gating device is switching fluid flow from the detector to the exhaust port or vice versa.

Conveniently, a power source is also provided. For example, batteries or other power cells. Preferably, the power source is formed integrally with the analyser.

According to a third aspect of the invention, a method of chemical detection comprises the steps of; (a) taking a molecular single electron transistor comprising at least one organic molecule attached to a drain electrode and a source electrode wherein, in use, said at least one organic molecule provides a quantum confinement region and (b) providing at least one analyte receptor site in the vicinity of said at least one organic molecule for receiving analytes. Preferably, the method further comprises the step of (c) measuring the electrical characteristics of said molecular single electron transistor to determine the presence or otherwise of an analyte. Conveniently, the method further comprises the step of passing a fluid over the at least one analyte receptor site.

According to a fourth aspect of the present invention, a carrier for a molecular single electron transistor device is characterised by the carrier comprising a first layer of material to provide a source electrode and a second layer of material to provide a drain electrode wherein said first and second layers of material sandwich, and are spaced apart by, a third layer of substantially insulating material.

Preferably, the carrier is arranged such that at least one organic molecule can be attached to the drain and source electrodes. Advantageously, the source and drain electrodes are spaced apart by a distance substantially equal to the length of the at least one organic molecule.

A molecular single electron transistor (MSET) detector device can thus be provided by said carrier when at least one organic molecule is attached to said source and drain electrodes of the carrier wherein, in use, said at least one organic molecule is arranged provide a quantum confinement region. In other words, a molecular single electron transistor device is provided that comprises at least one organic molecule attached to a drain electrode and a source electrode wherein, in use, said at least one organic molecule provides a quantum confinement region, characterised in that a first layer of material provides the source electrode and a second layer of material provides the drain electrode wherein said first and second layers of material sandwich, and are spaced apart by, a third layer of substantially insulating material.

In this manner, a CMOS based single electron transistor may be provided having source and drain electrodes held in spaced relation, said source and drain electrodes being adapted such that each end of a rod shaped organic molecule may be attached thereto. Attachment of an appropriate molecule to such a structure allows an MSET detector of the type described above to be readily fabricated.

According to a fifth aspect of the invention, a molecular single electron transistor (MSET) detector device comprises at least one organic molecule attached to a drain electrode and a source electrode wherein, in use, said at least one organic molecule provides a quantum confinement region characterised in that at least one of said source electrode and said drain electrode comprise, or consist of, a semiconductor material. Preferably, the semiconductor material is heavily doped. Source and drain electrodes formed from such a semiconductor material are stable at room temperature. This should be contrasted to the gold source and drain electrodes of the MSET described by Kubatkin et al (ibid) that decompose at temperatures greater than 150 Kelvin.

According to a sixth aspect of the invention, a method of forming a molecular single electron transistor comprises the steps of (i) forming source and drain electrodes and (ii) locating an organic molecule between said source and drain electrodes, characterised in that the source and drain electrodes are formed using a complementary metal oxide (CMOS) process. CMOS processing is well established thereby allowing MSET devices to be readily and reproducibly fabricated as described above.

BRIEF DESCRIPTION OF THE DRAWINGS

The invention will now be described, by way of example only, with reference to the following drawings in which;

FIG. 1 shows a schematic view of a gas analyser of the present invention,

FIG. 2 shows the pre-concentrator of the gas analyser system,

FIG. 9 shows a schematic diagram of the receptor portion of the MSET (FIG. 9a) and a band structure representation of the device (FIG. 9b), FIG. 10 illustrates the 2D conductance maps for a conventional SET (FIG. 10a) and a MSET (FIG. 10b)

DETAILED DISCUSSION OF EMBODIMENTS

Figure 3:
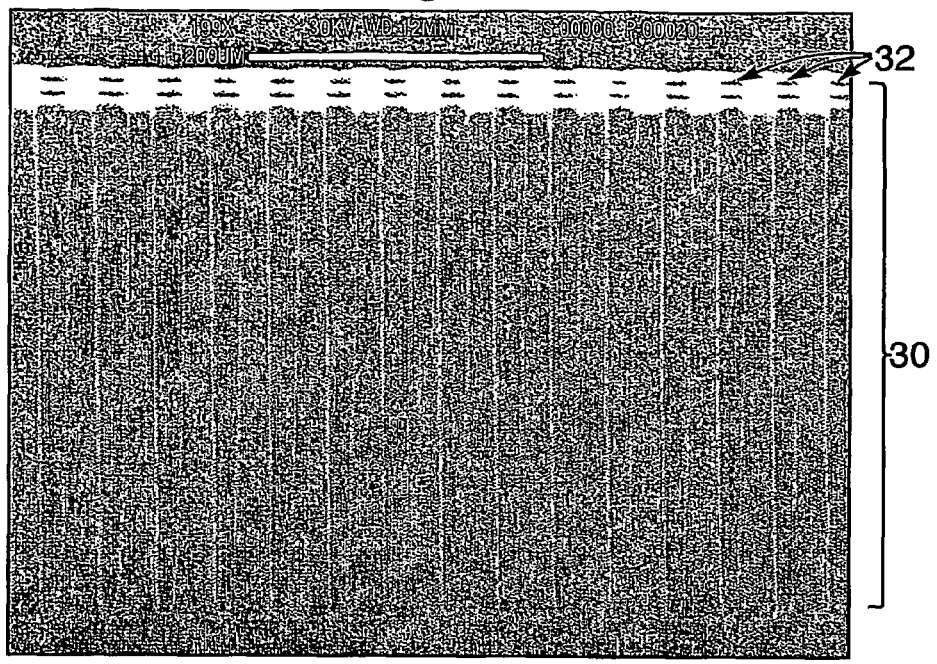
FIG. 3 shows a cross-sectional view of vias etched in a silicon wafer.

Referring to FIG. 1, a gas analyser 2 of the present invention is shown. The analyser 2 is formed as multi-layer hybrid structure, or MEMS cube, and comprises a pre-concentrator layer 4, a gating layer 6 and a detector layer 8.

The pre-concentrator 4 consists of a honeycombed silicon wafer and performs the function of pre-concentrating. The internal surfaces of the through-wafer vias of the honeycomb layer are coated with a trapping layer for molecules of interest and the low thermal mass structure is heated by integral resistive heater elements. The gating layer 6 comprises an electro-thermally operated MEMS shutter 10 that allows gas to be directed to either an exhaust port 12 or to the detector layer 8.

The detector layer 8 comprises a Molecular Single Electron Transistor (MSET) detector 14 integrated onto a silicon-ASIC chip. The MSET detector comprises a conjugated organic rod to form the quantum dot region. This is joined to silicon electrodes via tunnel barriers thereby giving rise to quantum confinement in the dot region. In a detection event, the molecule of interest will bind to an appropriate receptor attached to the organic quantum dot. The binding of just a single molecule to a receptor should give rise to measurable changes in the conductance properties of the device at room temperature.

In use, the apparatus initially adopts the molecule collection arrangement shown in FIG. 1a. In this configuration, the gas of interest is passed through the pre-concentrator 4 and directed out of the exhaust port 12. Any molecules of interest will bind to the trapping layer of the pre-concentrator 4.

After a certain sampling period, the MEMS shutter 10 is moved such that the analyser adopts the arrangement shown in FIG. 1b. The heaters of the pre-concentrator 4 are then used to heat the trapping layer and any molecules of interest are released therefrom. These released molecules are then directed, via the gating layer 6, to the detector layer 8 where they can be detected by the MSET detector 14.

It should be noted that each of the individual layers forming the stack will require alignment with respect to one another. The pre-concentrator and gas gating chips can utilize conventional bonding techniques, as these chips will be tolerant to thermal treatments. The detector chip, containing (thermally sensitive) electronics and the MSET are bonded using a low temperature polymer-based bonding technique. It is estimated that the integrated system's energy consumption per layer per measurement will be: less than 100 mJ for the pre-concentration, less than 100 mJ for the gas gating structure and less than 350 mJ for the detection circuitry. Thus, the estimated total energy per measurement is less than 1 J excluding the energy required to flow the sample through the device.

The analyser of the present invention offers a number of advantages over prior art systems. For example, the analyser could be fabricated to be around 2 $cm^3$ in size and is thus considerably smaller than prior art devices. However, despite the smaller size, the device can offer up to a one hundred-fold increase in sensitivity for the detection of certain molecular species as compared with known mass spectrometer systems. The inherent design of the cube can also reduce vapor dead space and should enhance detector sensitivity for more reliable detection with fewer false readings. In addition, the MEMS components are highly mechanically robust.

Detailed descriptions of the various layers forming the gas analyser are provided below. Although the combination of the described pre-concentrator, gating structure and MSET provide an analyser with the advantages described above, the skilled person would recognise that any one or more of these components may advantageously be used in a gas analysis system.

The Pre-concentrator

Referring to FIG. 2, a pre-concentrator 20 of the present invention is shown. The pre-concentrator comprises a honeycomb region 22 supported on a glass carrier 24. For a gas analyser of the type described above, the honeycomb region is typically 0.5 mm square. However, the skilled person would appreciate that the size and/or shape of the region 22 can be chosen as required for the particular application.

Figure 4:
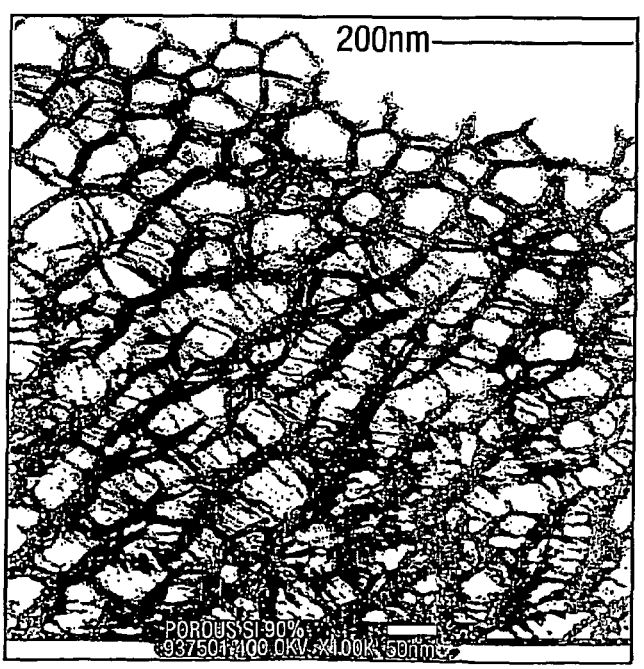
FIG. 4 shows a TEM image of highly porous silicon.

The honeycomb region 22 is fabricated from silicon, patterned using high aspect ratio DRIE (deep reactive ion etching). This process technology allows a rugged honeycomb type structure to be realised with a low thermal mass, several square millimetres surface area and good flow characteristics. Holes having a pitch of 40 µm and a diameter of 20 µm can be readily formed using such a technique; FIG. 3 is a photomicrograph of such holes (or vias) 32 formed in a silicon wafer 30. The inner surface of the vias 32 may also be porosified using, for example, stain etching or anodisation to further enhance the surface area in contact with the sample vapor. FIG. 4 shows an example of such a high surface area porosified material. Porosification will increase the surface area by a factor of around one hundred and can also allow a suitable adsorbing surface chemistry to be created at the surface.

The holes 32 may be lined with a variety of appropriate chemical layers or a given surface treatment (e.g. self-assembled monolayers) may be applied. The various linings or treatments that may be applied to the holes, for example a stable hydrophobic or hydrophilic coating, may be arranged to selectively trap only certain molecule(s) of interest. The person skilled in the art would be aware of the various layers/treatments that can be used to trap molecules for various applications.

In the device shown in FIG. 2, conductive p-type silicon is used to form the honeycomb region 22. This allows the silicon structure of the honeycomb to form a resistive heater thereby removing the requirement for metal heater tracks. This arrangement also provides accurate temperature control thereby increasing desorption selectivity. Polysilicon or platinum layers may alternatively or additionally be included in the structure to form a resistive heater or integrated temperature sensors; these layers may be formed on the top surface of the wafer and/or integrated into the vertical holes. It should be noted that the honeycomb structure may be formed in a variety of alternative materials; for example other semi-conductor materials, or in micro-moulded plastic.

Although by no means essential, the honeycomb region 22 may be mounted on a glass carrier 24. The glass carrier 24 may be patterned (e.g. with trenches 26) to both limit the thermal heat loss from the pre-concentrator and to allow fluidic communication through the plane of the device to any substrates below. The high thermal conductivity of the silicon, relative to the glass carrier, helps ensure that the uniformity of heating is high across the active area of the pre-concentrator. The exact structure of the pre-concentrator can, of course, be optimised for best thermal performance for a given application.

Figure 5:
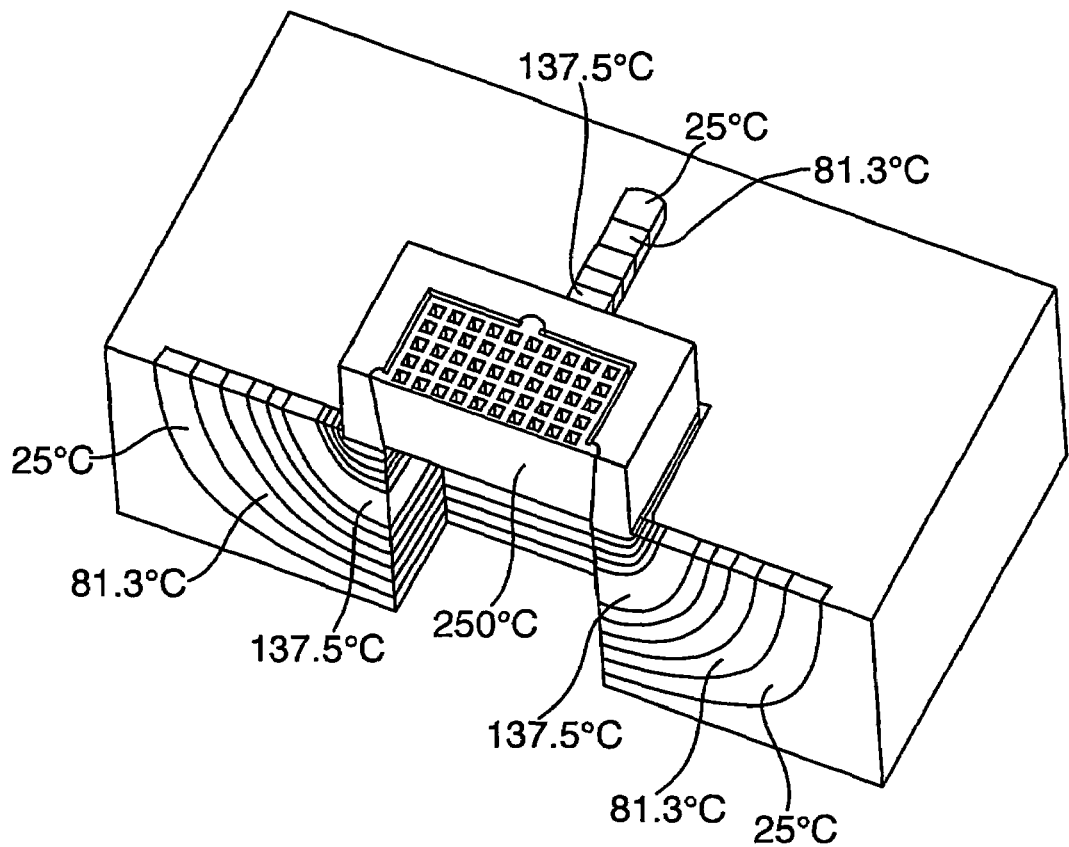
FIG. 5 shows the modelled temperature distribution of the pre-concentrator of FIG. 2.

FIG. 5 shows the predicted temperature profile of a pre-concentrator structure of the type shown in FIG. 2 for one set of conductances. Table 1 also outlines the thermal properties of a pre-concentrator of the type described above.

TABLE 1

Parameters and modelled performance for a 0.5 mm by 0.5 mm pre-concentrator honeycomb.

| Parameter | Value |
| --- | --- |
| Silicon thickness | 150 μm |
| Hole pitch | 50 μm |
| Hole size | 30 μm |
| Silicon volume | 0.054 mm$^3$ |
| Glass thickness | 500 μm |
| Bond contact area | 0.271 mm$^2$ |
| Honeycomb footprint | 0.25 mm$^2$ |
| Active adsorbing area (neglecting effects of porosification) | 2.1 mm$^2$ |
| Thermal time constant | 120 ms |
| Input power | 250 mW |
| Time to rise 200 K | 110 ms |
| Energy consumption | 0.03 J |

The thickness and footprint of the pre-concentrator structure may be readily tuned to achieve an appropriate compromise between power budget, thermal response time and active area. For example, increasing the honeycomb footprint to 1 mm$^2$ yields an absorber area (untreated) of around 10 mm$^2$. Increasing the power applied to 0.5 W leads to a 200K rise time of around 120 ms, and an energy requirement of around 0.06 J It can thus be seen that the vertical architecture of the pre-concentrator of the present invention enables compact and practical integration, with the minimum dead volume, within a gas analyser device.

Gas Gating Structure

As described above with reference to FIG. 1, the gas gating structure is arranged to include a physical valve that enables gas to be directed along either one of two different routes. The first route permits a rapid gas flow through the device avoiding the gas detector and the second route allows gas flow from the pre-concentrator to be diverted to the detector chip. The second route is selected to coincide with the controlled release of the pre-concentrated agents from the pre-concentrator.

Figure 6A:
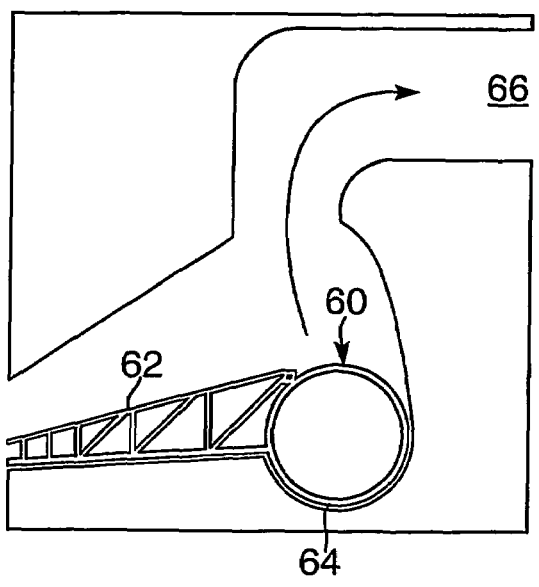
FIG. 6 shows the gas shutter of the gas detection system in an open (FIG. 6a) and closed (FIG. 6b) configuration.
Figure 6B:
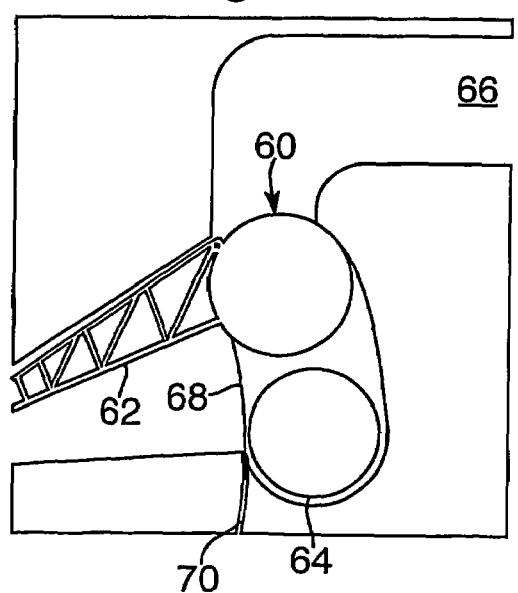

Referring to FIG. 6, a gas gating arrangement incorporating a substrate port 64, an exhaust port 66 and moveable MEMS shutter 60 is shown. The MEMS shutter 60 is supported on an armature 62. The armature is attached to a compliant displacement multiplier (not shown) which is in turn attached to a bent beam electrothermal actuator (not shown). The bent beam actuator applies a displacement to the compliant structure which displaces and rotates the armature 62. This allows the shutter 60 to move between the first position of FIG. 6a and the second position of FIG. 6b.

Gas from the pre-concentrator is incident on the gas gating arrangement in a direction perpendicular to the plane of the surface and along an axis co-incident with the axis of the substrate port 64. In the first position shown in FIG. 6a, the substrate port 64 is closed and gas passes along a first route and exits the gas gating arrangement via the exhaust port 66. In the second position shown in FIG. 6b, the exhaust port 66 is closed and gas passes along a second route and exits the gas gating arrangement via the substrate port 64.

A sealing arm 68, and a corresponding recess 70 in the substrate, are also provided. The sealing arm is arranged such that, when the shutter is in the second position of FIG. 6b, the amount of "dead-space" within the flow path is minimised by blocking gas flow into the hollow regions of the substrate in which the MEMS armature and actuator are formed. This ensures the maximum number of molecules of interest are passed to the detector.

The gas-gating structure is fabricated using deep reactive ion etching (DRIE) of 'through-wafer' silicon channels, and a DRIE step is used to form the micro-machined MEMS silicon shutter (valve) system on an SOI substrate.

The MEMS shutter arrangement shown in FIG. 6 can be readily provided with around 0.5 mm throw actuation. The MEMS shutter 60 can also be opened and closed within a few milliseconds thereby ensuring that gas flowing from the pre-concentrator to the sensor contains the maximum number of molecules of interest and the minimum amount of interferents. In the open position, the released molecules of interest will have line of sight access to the sensor; this is in contrast to the tortuous path through the prior art MEMS based valves that are described above.

The MEMS shutter arrangement of the present invention also has a power consumption of less than a watt. Furthermore, the use of an electro-thermal hold latch to fix the shutter in the open position when required minimises the average power consumption, and makes the device a suitable candidate for use in a system with a low energy budget. The energy required to open and latch the shutter is around 0.05 J, and zero power is required to hold the shutter in position. The voltage of operation can be tuned by selection of the dopant concentration in the material forming the electrothermal actuator.

The use of the MEMS shutter arrangement in a fluidic system enables a very large flow area. This enables higher rates of fluid flow in both open and closed positions compared with prior art diaphragm valve systems. When the shutter is in the closed position (i.e. gas directed to the exhaust port), the air may be routed around the shutter through a recess above the shuttered area at a relatively high pressure. Air flowing onto the shutter will tend to force it closed, and maintain a seal. When the shutter is in the open position (i.e. gas directed to the substrate port), the shutter blocks the path through the recess, and air is routed through the substrate port, directly onto the detector below. Again the action of the air pressure will help to seal the shutter, although a lower fluid flow rate is likely to be required when gas is directed to the detector. During switching between the open and closed states, the gas flow may be reduced to reduce the pressure on the shutter element.

Figure 7:
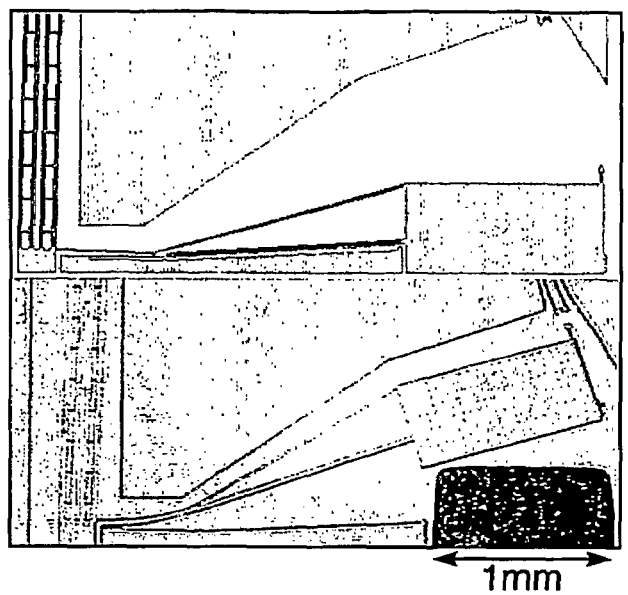
FIG. 7 shows an example of a gas shutter of the type described with reference to FIG. 6.

Referring to FIG. 7, examples of a shutter design in the open (FIG. 7b) and closed (FIG. 7a) positions is given. FIG. 7b is a photomicrograph of an SOI based device under actuation.

The MSET Detector

Figure 8:
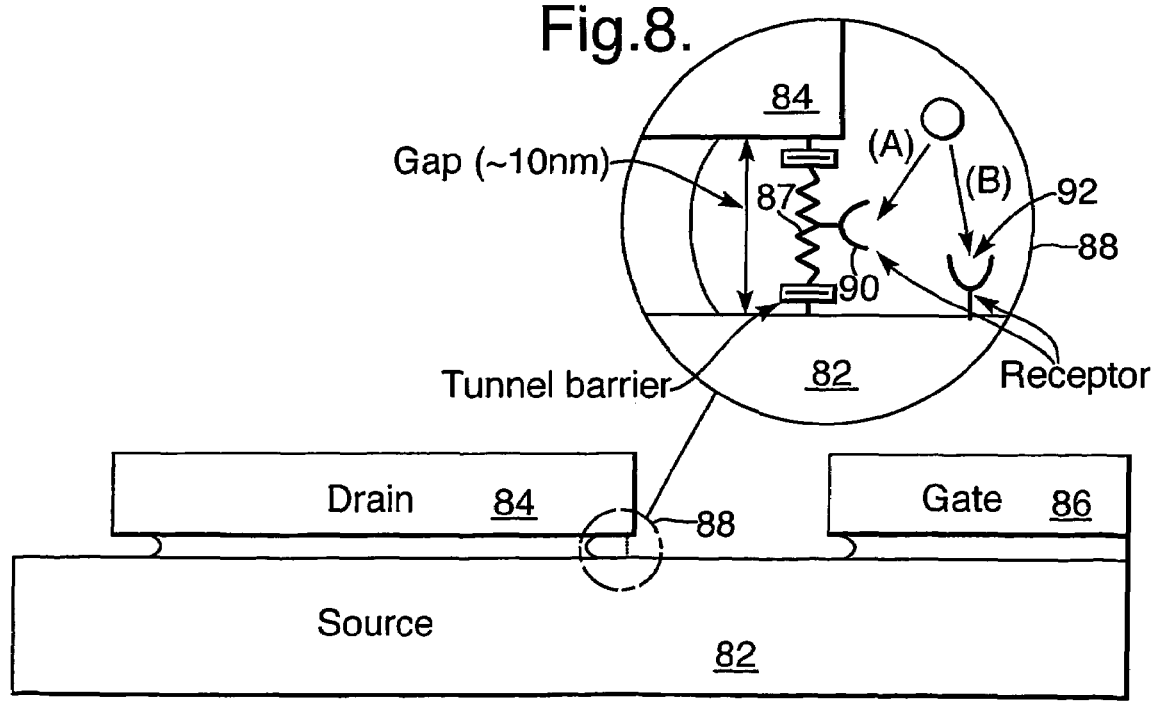
FIG. 8 is a schematic illustration of the molecular single electron transistor (MSET) detection device of the gas detection system.

Referring to FIG. 8, a schematic of a molecular single electron transistor (MSET) structure of the present invention, fabricated using CMOS device processing, is shown. The MSET comprises a silicon source electrode 82, a polysilicon drain electrode 84 and a polysilicon gate electrode 86. An active region 88 (shown in more detail in the FIG. 8 inset) comprises a self-assembled monolayer of organic molecules lying between the source and drain electrodes.

The organic molecules 87 of active region 88 comprise a conjugated organic rod (the quantum dot region) which is joined to silicon electrodes via tunnel barriers. This gives rise to quantum confinement in the dot region as described in more detail below. In operation, with a small source-drain bias, the gate is biased such that the single electron current from source to drain is at the steepest part of the transconductance curve.

A first binding site 90 is provided on the organic molecule 87 and/or a second site 92 is provided on the substrate. The presence of a single molecule of interest binding at the first site 90 or the second site 92 will lead to an observable change in source-drain current and hence detection. Further discrimination of the adsorbed molecule(s) is possible by analyzing I-V 'signatures', as discussed in more detail below, when both the source-drain and the gate biases are varied.

Referring now to FIG. 9a, a schematic representation of the active region of an MSET device of the invention is shown in more detail. The MSET structure can be conceptualised as a molecular semi-conducting core 100 located between two electronically insulating σ-bonded groups 102. A chemically active group 104 attached to this core will bind molecules of interest. Each end of the molecule 100 will be chemically bound to the silicon electrodes 106. FIG. 9b shows a band structure representation of the device shown in FIG. 9a in which ΔV represents the effect on the molecular states of small electrostatic perturbations (e.g. a docked molecule).

Conductivity through a SET can be controlled by both gate voltage ($V_g$) and source-drain voltage ($V_{DS}$). FIG. 10a illustrates the resultant conductivity map as a function of $V_g$ and $V_{DS}$ for a conventional SET exhibiting coulomb blockade.

An MSET device of the type describe herein shows additional structure that is specific to the electronic properties of the molecule; this is shown in FIG. 10b. This signature would be very sensitive to the details of the docked molecule and could be used to identify the adsorbed molecule. The molecular identification process can be aided using quantum mechanical calculation of the energy levels for the molecular backbone alone, and also for the backbone with the analyte (i.e. molecule of interest) attached. These energy levels can then be used to enhance orthodox theories of SET transport to predict I-V characteristics and conductance maps for MSETs. This enables unique identification of docked molecules, and will also guide the design and synthesis of backbone and receptor molecules.

A low noise amplifier is required to detect the small (pico-Amp) current displacements related to the detection events. Such an amplifier can be fabricated on a foundry 0.35 μm CMOS process. The detector circuit can be fabricated using the same CMOS (0.35 μm) process technology that is used to produce the electrode structure of the MSET. The MSET and amplifying circuitry can thus be fabricated in the same process flow and hence on the same silicon chip. In order to complete the fully integrated MSET device, post-processing will be required to open access windows in the CMOS passivation layers to the MSET support structure followed by introduction of the relevant organic molecules in the form of a self assembled monolayer. Differential measurements and provision of an array of detectors on a single chip is also possible.

The attachment of the active molecule to the silicon electrodes is accomplished by chemical bonding. The molecule is preferably attached at each end, so a di-functional, symmetric molecule is preferred. Various attachment options would be apparent to a person skilled in the art, for example:

(i) Oxidation of the silicon surface to silicon dioxide will provide a surface suitable for docking with trialkoxy silane groups. This chemistry is well established and allows the formation of dense self-assembled monolayers of molecules. It is straightforward to apply this technique to fabricate sparse arrays of active molecules for SETs.

(ii) Chlorination of the silicon surface provides an array of active Si—Cl bonds which can be reacted with organic amines to provide a tightly bound layer. Assembly of dense layers of aliphatic and aromatic amines can be achieved, and the method has the advantage that the organic amines are relatively easy synthesis targets.

(iii) Reaction of a silicon surface with an organolithium reagent or Grignard reagent provides a route to surface bound organic molecules. The reaction can be facilitated by chlorination of the surface, or electrochemically.

(iv) Organic alkenes can be bound to silicon having Si—H surface groups by a hydrosilylation reaction.

The above options encompass a wide range of organic materials and surface treatment conditions; the choice of which to use will be determined by ease of synthesis of the molecule and compatibility of the process with all the materials and the various structures present.

Figure 11:
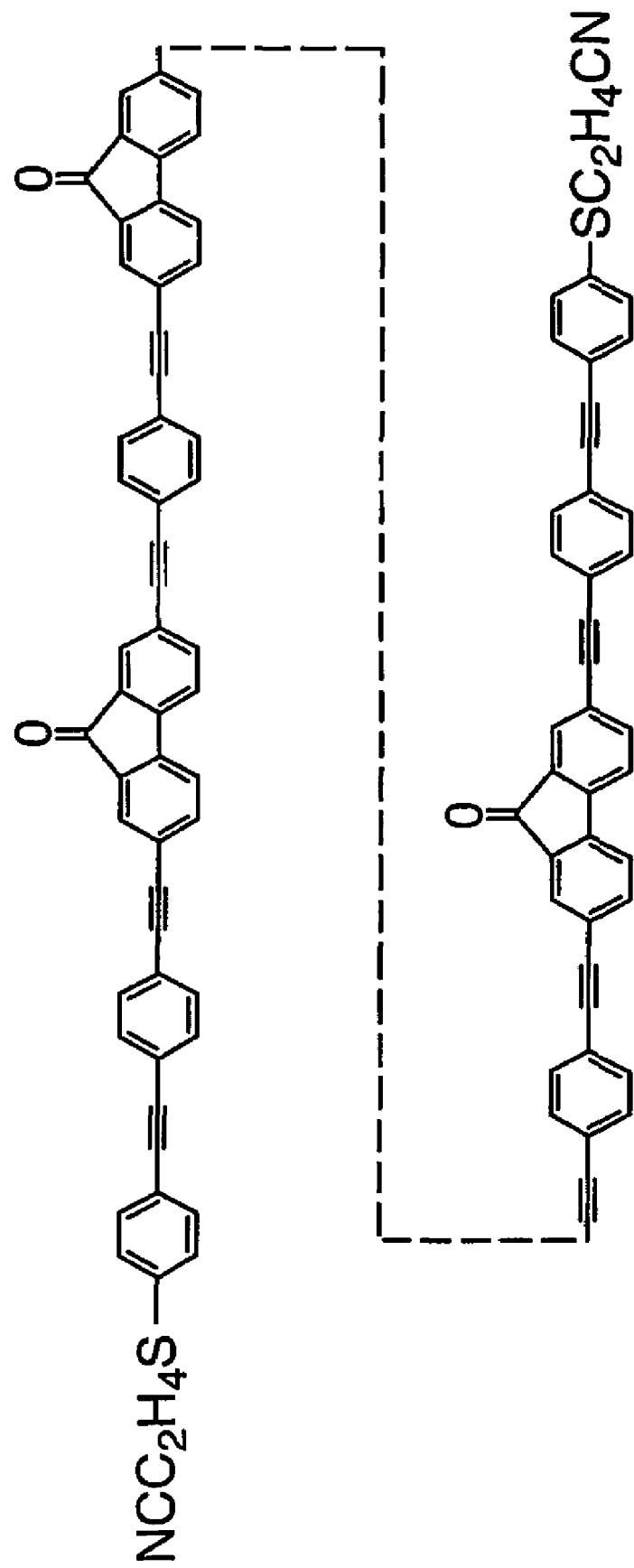
FIG. 11 shows a molecule "T" that can form the basis of the molecule used in the MSET of FIGS. 8 to 10.

The molecule attached to the SET is preferably a rod-shaped molecular wire of length sufficient to bridge the CMOS gate oxide thickness. The molecule shown in FIG. 11, hereafter referred to as molecule "I", represents a molecule that can form the basis of the molecule that is used. This molecule (I) has already been synthesised in excellent purity and high yield for docking onto gold electrodes. The length of the molecule is 6.8 nm. Lateral substituent groups are provided to maintain its solubility, but are omitted for clarity. Molecule (I) has an appropriate molecular length, reversible electrochemical doping (reduction) even in solution, and functional groups at each end for attachment to a surface. Further work has demonstrated that functional groups can be attached laterally to (I) to provide a receptor site for chemical sensing.

Various changes are required to molecule I to make it suitable for use in a SET. Firstly, the molecular rod is modified to provide electronically insulating units at each end; alicyclic units such as 2,2,2-bicyclooctane provide candidate units which maintain the rigidity of the structure. The end groups are also altered to make them suitable to bind to silicon, rather than gold. Chemical receptor units tailored to selectively bind the molecules of interest are incorporated. The molecular length is also tailored to match the gate oxide thickness accurately; this facilitates docking on the electrodes in a unique environment. It is well known that molecular length can be controlled at the synthesis stage in increments of 0.2-0.3 nm by adding atoms, and on a finer scale by exchange of chemical groups for ones having slightly longer or shorter bond lengths.

By adding a receptor incorporating a nucleophilic group, the MSET will bind fluorophosphonate agents, e.g. pesticides, by nucleophilic displacement of F. Further discrimination can be provided by having an array of MSET detectors with different receptors attached to the backbone molecules. Pattern recognition techniques may be employed to analyse the measured conductance properties of the MSET thereby allowing analytes to be identified.

During fabrication of the MSET, photoelectron spectroscopy can be used to provide a sufficiently sensitive probe to monitor deposition of the organic material on the electrode surfaces, and allow the degree of coverage to be evaluated. Alternatively, the conductance may be monitored in situ.

The invention claimed is:

1. A molecular single electron transistor (MSET) detector device comprising at least one organic molecule attached to a drain electrode and a source electrode wherein a first layer of material provides the source electrode and a second layer of material provides the drain electrode, said first and second layers are spaced apart by a third layer of substantially insulating material, where at least one of said first and second layers is comprised of a silicon semiconductor, wherein, said at least one organic molecule provides a quantum confinement region and at least one analyte receptor site is provided in the vicinity of said at least one organic molecule.

2. A device according to claim 1 wherein the at least one organic molecule provides at least one analyte receptor site.

3. A device according to claim 1 wherein at least one analyte receptor site is located adjacent, but is not attached to, said at least one organic molecule.

4. A device according to claim 1 wherein said at least one organic molecule is an elongated conjugated organic molecule having first and second ends, the first end being attached to the source electrode and the second end being attached to the drain electrode.

5. A device according to claim 1 wherein a single organic molecule is attached to the source electrode and the drain electrode.

6. A device according to claim 1 wherein said at least one organic molecule is attached to the source and drain electrodes via tunnel barriers.

7. A device according to claim 6 wherein the tunnel barriers are provided by electrically insulating regions of said at least one organic molecule.

8. A device according to claim 6 wherein the source and drain electrodes each comprise an insulating material that forms said tunnel barriers.

9. A device according to claim 1 and further comprising a gate electrode.

10. A device according to claim 9 wherein the first layer of material comprises a silicon wafer, the second layer of material comprises polysilicon and the third layer of substantially insulating material comprises a silicon oxide.

11. A device according to claim 10 wherein the wafer additionally carries a layer of polysilicon to form the gate electrode, the fourth layer being separated from the silicon wafer by a layer of silicon oxide.

12. A device according to claim 10 that is formed using a process that comprises a complementary metal oxide semiconductor (CMOS) fabrication process.

13. A device according to claim 1 wherein a recess is provided in the third layer of substantially insulating material to provide a region between the source and drain electrodes in which the at least one organic molecule is located.

14. A device according to claim 1 wherein the thickness of the third layer of substantially insulating material is substantially equal to the length of the at least one organic molecule.

15. A device according to claim 1 wherein the at least one organic molecule comprises end chains that will bind to silicon.

16. A device according to claim 1 and further comprising means for measuring the conductivity of the at least one organic molecule as a function of applied source-drain voltage.

17. A device according to claim 1 and further comprising means for measuring the conductivity of the at least one organic molecule as a function of applied gate voltage.

18. A device according to claim 1 and further comprising integral electronic circuitry for measuring the conductivity of the at least one organic molecule.

19. A fluid analyser comprising an MSET device according to claim 1.

20. An analyser according to claim 19 and further comprising a pre-concentrator for releaseably retaining analytes from a fluid.

21. An analyser according to claim 20 wherein the pre-concentrator comprises a layer of material having a plurality of apertures through which a fluid can be passed, the internal surfaces of said apertures being adapted to releaseably retain analytes from the fluid.

22. An analyser according to claim 21 wherein the internal surfaces defining said plurality of apertures of the pre-concentrator are porosified.

23. An analyser according to claim 21 wherein the layer of material from which the pre-concentrator is formed comprises a layer of silicon, said apertures being formed through said layer of silicon and arranged to form a honeycomb structure.

24. An analyser according to claim 21 wherein the internal surfaces of the apertures of the pre-concentrator are reversibly adsorptive.

25. An analyser according to claim 20 wherein the pre-concentrator comprises a heater.

26. An analyser according to claim 20 and further comprising a fluid gating structure for controlling the flow of fluid from the pre-concentrator to the MSET device.

27. An analyser according to claim 26 wherein the fluid gating structure is arranged to selectively route fluid from the pre-concentrator to either one of the MSET device and an exhaust port.

28. An analyser according to claim 26 wherein the fluid gating structure comprises a substantially planar substrate and a shutter that is moveable in the plane of said substrate.

29. An analyser according to claim 26 wherein fluid is routed from the fluid gating structure to the MSET device along a channel having a long axis that is substantially perpendicular to the plane of the substantially planar substrate of the fluid gating structure.

30. An analyser according to claim 26 wherein the fluid gating structure comprises a shutter that is shaped such that it can engage and seal the entrance to said channel.

31. An analyser according to claim 30 wherein the shutter is a micro-electromechanical (MEMS) shutter.

32. An analyser according to claim 31 wherein the fluid gating structure comprises a MEMS electro-thermal actuation mechanism to impart movement to the MEMS shutter.

33. An analyser according to claim 32 wherein the fluid gating structure further comprises a MEMS compliant displacement mechanism.

34. An analyser according to claim 26 wherein the pre-concentrator, fluid gating device and MSET device are formed as substantially planar layers and are arranged in a stack.

35. An analyser according to claim 34 wherein each substantially planar layer comprises silicon.

36. An analyser according to claim 19 and further comprising a fluid pump.

37. An analyser according to claim 19 and further comprising an integral power source.

38. A plurality of MSET devices according to claim 1, wherein said devices are arranged in an array, each of said devices having an organic molecule and different receptors are attached to each molecule.

39. An analyser comprising a fluid analyzer and a pre-concentrator for releasably retaining analytes from a fluid including an MSET device comprised of at least one organic molecule attached to a drain electrode and a source electrode, wherein, said at least one organic molecule provides a quantum confinement region and at least one analyte receptor site is provided in the vicinity of said at least one organic molecule, wherein a shutter may be retained, without the application of power, in an open position in which fluid is routed from the pre-concentrator to the MSET device or in a closed position in which fluid is routed from the pre-concentrator to an exhaust port.

40. A method of chemical detection comprising the steps of:
    (a) taking a molecular single electron transistor comprising at least one organic molecule attached to a drain electrode and a source electrode, said electrodes spaced apart by a substantially insulating layer, wherein at least one of the source and drain electrodes comprises a silicon semiconductor and wherein, said at least one organic molecule provides a quantum confinement region; and
    (b) providing at least one analyte receptor site in the vicinity of said at least one organic molecule for receiving analytes.

41. A method of chemical detection according to claim 40 and further comprising the step of (c) measuring the electrical characteristics of said molecular single electron transistor to determine the presence or otherwise of an analyte.

42. A method of chemical detection according to claim 40 and further comprising the step of passing a fluid over the at least one analyte receptor site.

43. A molecular single electron transistor (MSET) detector device comprising at least one organic molecule attached to a drain electrode and a source electrode wherein, in use, said at least one organic molecule provides a quantum confinement region wherein at least one of said source electrode and said drain electrode are formed from silicon semiconductor material and are spaced apart by a substantially insulating material, wherein at least one analyte receptor site is provided in the vicinity of said at least one organic molecule.

44. A method of forming a molecular single electron transistor comprising the steps of (i) forming source and drain electrodes and (ii) locating an organic molecule between said source and drain electrodes, wherein the source and drain electrodes are formed using a complementary metal oxide (CMOS) process, and wherein at least one of said source and drain electrodes are formed from silicon semiconductor and are spaced apart by a substantially insulating layer, wherein at least one analyte receptor site is provided in the vicinity of said at least one organic molecule.

45. A molecular single electron transistor (MSET) detector device comprising at least one organic molecule attached to a drain electrode and a source electrode wherein
    said at least one organic molecule provides a quantum confinement region and at least one analyte receptor site is located adjacent, but is not attached to, said at least one organic molecule.

* * * * *